US012594315B2

(12) United States Patent
Ma et al.

(10) Patent No.: US 12,594,315 B2
(45) Date of Patent: Apr. 7, 2026

(54) USE OF *Liriodendron chinense (Hemsl.) Sarg.* OR EXTRACT THEREOF IN THE PREPARATION OF MEDICAMENT FOR REDUCING SERUM URIC ACID LEVEL AND PREVENTING AND TREATING URIC ACID NEPHROPATHY

(71) Applicant: SICHUAN CREATION PHARMACEUTICAL TECHNOLOGY CO., LTD., Chengdu (CN)

(72) Inventors: Liang Ma, Chengdu (CN); Ping Fu, Chengdu (CN)

(73) Assignee: SICHUAN CREATION PHARMACEUTICAL TECHNOLOGY CO., LTD. (CN)

( * ) Notice: Subject to any disclaimer, the term of this patent is extended or adjusted under 35 U.S.C. 154(b) by 709 days.

(21) Appl. No.: 17/767,492

(22) PCT Filed: Oct. 23, 2020

(86) PCT No.: PCT/CN2020/123257
    § 371 (c)(1),
    (2) Date: Apr. 8, 2022

(87) PCT Pub. No.: WO2021/078252
    PCT Pub. Date: Apr. 29, 2021

(65) Prior Publication Data
    US 2024/0316137 A1     Sep. 26, 2024

(30) Foreign Application Priority Data
    Oct. 24, 2019   (CN) .......................... 201911017671.8

(51) Int. Cl.
    *A61K 36/57*       (2006.01)
    *A61P 13/12*       (2006.01)
(52) U.S. Cl.
    CPC .............. *A61K 36/57* (2013.01); *A61P 13/12* (2018.01); *A61K 2236/333* (2013.01); *A61K 2236/51* (2013.01)

(58) Field of Classification Search
    CPC .................................................... A61K 36/57
    See application file for complete search history.

(56) References Cited

U.S. PATENT DOCUMENTS 4,093,717 A     6/1978  Hufford
6,582,735 B2 *  6/2003  Stogniew ............... A61K 36/57
                                              424/769

FOREIGN PATENT DOCUMENTS

CN     108601847 A     9/2018
KR     20040033983 A   4/2004
KR     20140140346 A   12/2014

OTHER PUBLICATIONS

Tsushima Y et. al. (Uric acid secretion from adipose tissue and its increase in obesity, J Biol Chem. Sep. 20, 2013;288(38):27138-27149). (Year: 2013).*
Muhammad Akram, "Comprehensive review on therapeutic strategies of gouty arthritis", Pakistan Journal of Pharmaceutical Sciences, vol. 27, No. 5, Sep. 30, 2014, pp. 1578-1579.
Jing Pan, "Ethanol extract of *Liriodendron chinense (Hemsl.) Sarg barks* attenuates hyperuricemic nephropathy by inhibiting renal fibrosis and inflammation in mice," Journal of Ethnopharmacology 264 (2021) 113278.

* cited by examiner

*Primary Examiner* — Terry A McKelvey
*Assistant Examiner* — Jacob A Boeckelman
(74) *Attorney, Agent, or Firm* — Emerson, Thomson & Bennett, LLC; Roger D. Emerson; Peter R. Detorre

(57)                    ABSTRACT
The present disclosure relates to the field of medicaments, and particularly to use of *Liriodendron chinense* (Hemsl.) Sarg, or an extract thereof in the preparation of a medicament for reducing a serum uric acid level and preventing and treating uric acid nephropathy, and belongs to the field of medicaments. In one aspect, the present disclosure provides use of *Liriodendron chinense* (Hemsl.) Sarg. or an extract thereof in the preparation of a medicament for reducing a serum uric acid level. In another aspect, the present disclosure further provides use of *Liriodendron chinense* (Hemsl.) Sarg. or an extract thereof in the preparation of a medicament for treating and/or preventing uric acid nephropathy.

14 Claims, 2 Drawing Sheets

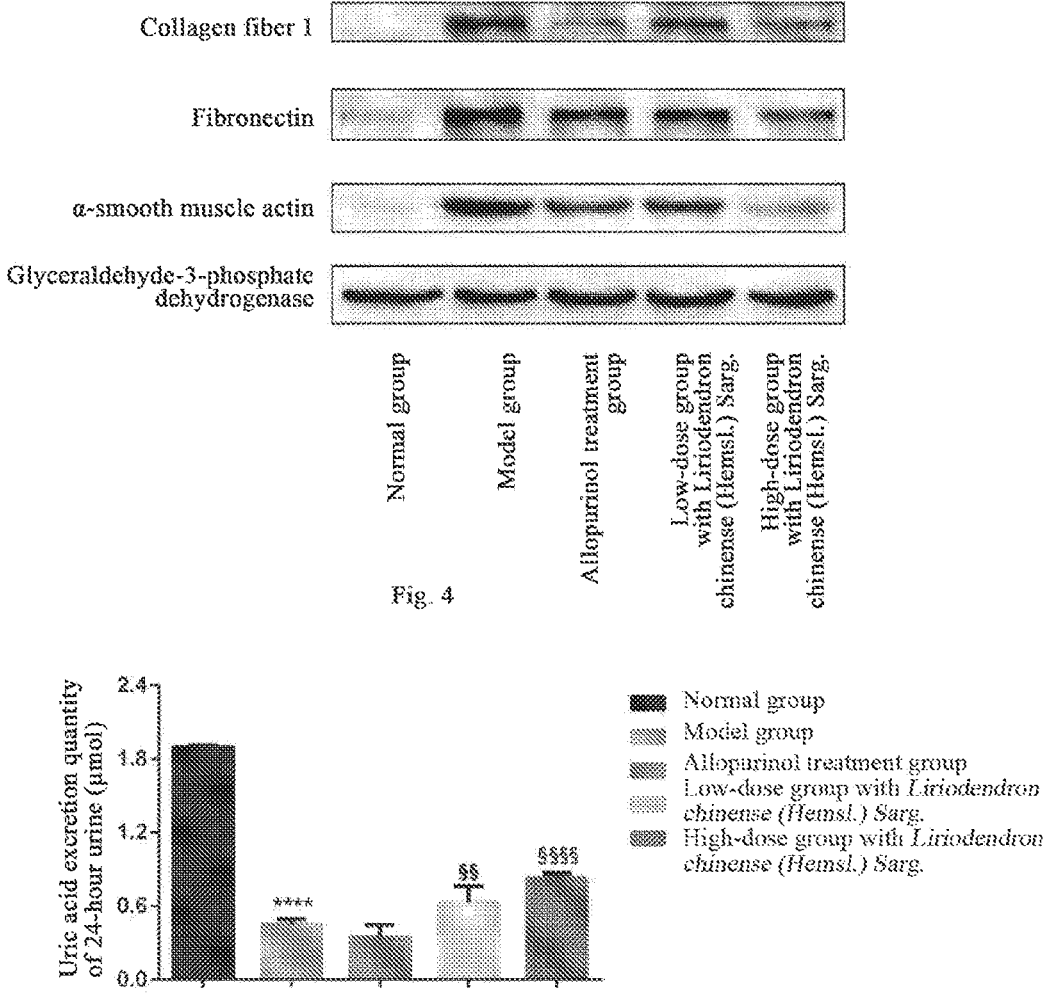

Collagen fiber 1

Fibronectin

α-smooth muscle actin

Glyceraldehyde-3-phosphate
dehydrogenase

Normal group

Model group

Allopurinol treatment group

Low-dose group with Liriodendron chinense (Hemsl.) Sarg.

High-dose group with Liriodendron chinense (Hemsl.) Sarg.

Fig. 4

Uric acid excretion quantity of 24-hour urine (μmol)

Normal group
Model group
Allopurinol treatment group
Low-dose group with *Liriodendron chinense (Hemsl.) Sarg.*
High-dose group with *Liriodendron chinense (Hemsl.) Sarg.*

USE OF *Liriodendron chinense (Hemsl.) Sarg.* OR EXTRACT THEREOF IN THE PREPARATION OF MEDICAMENT FOR REDUCING SERUM URIC ACID LEVEL AND PREVENTING AND TREATING URIC ACID NEPHROPATHY This disclosure is a U.S. National Stage Application [under 35 U.S.C. sec. 371]of International Application No. PCT/CN2020/123257, filed on Oct. 23 2020, which claims priority to Chinese Patent Application no. 201911017671.8, filed with the China National Intellectual Property Administration (CNIPA) on Oct. 24, 2019, the contents of which are incorporated herein by reference in their entirety.

TECHNICAL FIELD

The present disclosure relates to the field of medicaments, and particularly to use of *Liriodendron chinense* (Hemsl.) Sarg. or an extract thereof in the preparation of a medicament for reducing a serum uric acid level and preventing and treating uric acid nephropathy.

BACKGROUND

Hyperuricemia refers to the condition that. with normal-purine diet, the fasting serum uric acid level measured twice on different days is above 416 μmol/L (7 mg/dl) for men and above 357 μmol/L (6 mg/dl) for women. In recent years, many studies at home and abroad have confirmed that the hyperuricemia is closely related to the occurrence and development of gout, cardiovascular diseases, metabolic syndrome, hypertension, and kidney diseases. The hyperuricemia is an important cause of the increased prevalence rate of Chronic Kidney Disease (CKD) and is an independent risk factor for CKD progression. Studies have shown that reducing of the serum uric acid level can delay the progression of kidney diseases. Preventing and correcting the hyperuricemia, reducing the serum uric acid level, and preventing urate deposition in the kidney are of great importance in the treatment of hyperuricemic nephropathy.

*Liriodendron chinense* (Hemsl.) Sarg., also known as Chinese Tulip Tree, is a plant belonging to the genus *Liriodendron* of the family Magnoliaceae. According to the literatures, bark of the *Liriodendron chinense* (Hemsl.) Sarg. have the effects of dispelling wind and eliminating dampness, relieving a cough, treating rheumatic joint pains and the like. But whether it has the effects of reducing the serum uric acid level and relieving uric acid nephropathy has not yet been reported.

SUMMARY

The present disclosure aims to solve at least one of the technical problems existing in the prior art. Therefore, the objective of the present disclosure is to provide use of *Liriodendron chinense* (Hemsl.) Sarg. or an extract thereof in the preparation of a medicament for reducing a serum uric acid level. Another objective of the present disclosure is to provide use of *Liriodendron chinense* (Hemsl.) Sarg. or an extract thereof in the preparation of a medicament for treating and/or preventing uric acid nephropathy.

The present disclosure provides use of *Liriodendron chinense* (Hemsl.) Sarg. or an extract thereof in the preparation of a medicament for reducing a serum uric acid level.

The present disclosure provides use of *Liriodendron chinense* (Hemsl.) Sarg. or an extract thereof in the preparation of a medicament for treating and/or preventing gout.

The present disclosure provides use of *Liriodendron chinense* (Hemsl.) Sarg. or an extract thereof in the preparation of a medicament for treating and/or preventing uric acid nephropathy.

Further, the use satisfies at least one of the following:

the medicament reduces a level of at least one of serum creatinine, serum uric acid, blood urea nitrogen, or urine microalbumin;

the medicament relieves renal tubular dilation and/or glomerulosclerosis;

the medicament relieves renal fibrosis; or the medicament reduces an expression quantity of at least one of collagen fiber 1, fibronectin, or α-smooth muscle actin in a kidney.

Further, the medicament promotes renal uric acid excretion.

Further, the medicament is a formulation prepared by using the *Liriodendron chinense* (Hemsl.) Sarg. or the extract thereof as an active ingredient and adding pharmaceutically acceptable adjuvants or auxiliary ingredients.

Further, the formulation is an oral formulation or an injectable formulation.

Further, a medicinal part of the *Liriodendron chinense* (Hemsl.) Sarg. is at least one of roots, bark, branches, or leaves.

Further, the extract is an alcohol extract and/or water extract.

Preferably, the alcohol is $C_1$ to $C_6$ fatty alcohol.

Further preferably, the alcohol is ethanol.

Further, the method for preparing the extract includes the following steps: adding the *Liriodendron chinense* (Hemsl.) Sarg. into an aqueous ethanol solution for extraction, and concentrating the extracting solution, thus obtaining the extract.

Further, the extraction satisfies at least one of the following:

adding into 75% v/v aqueous ethanol solution for extraction;

allowing the solid-liquid ratio to be 500 g/5 L; or performing the extracting for 3 hours under a boiling condition.

The present disclosure provides *Liriodendron chinense* (Hemsl.) Sarg. or an extract thereof for reducing a serum uric acid level.

The present disclosure provides *Liriodendron chinense* (Hemsl.) Sarg. or an extract thereof for treating and/or preventing gout.

The present disclosure provides *Liriodendron chinense* (Hemsl.) Sarg. or an extract thereof for treating and/or preventing uric acid nephropathy.

The present disclosure provides a method for reducing a serum uric acid level, including administering a subject in need thereof *Liriodendron chinense* (Hemsl.) Sarg. or an extract thereof for.

The present disclosure provides a method for treating and/or preventing gout, including administering a subject in need thereof *Liriodendron chinense* (Hemsl.) Sarg. or an extract thereof.

The present disclosure provides a method for treating and/or preventing uric acid nephropathy, including administering a subject in need thereof *Liriodendron chinense* (Hemsl.) Sarg. or an extract thereof.

The present disclosure provides the use of the *Liriodendron chinense* (Hemsl.) Sarg. or the extract thereof in the preparation of the medicament for reducing the serum uric acid level and preventing and treating the uric acid nephropathy. Animal experiments have confirmed that the *Liriodendron chinense* (Hemsl.) Sarg. can significantly reduce the serum uric acid level, and relieve degrees of renal tubular dilation, glomerulosclerosis and renal interstitial fibrosis of hyperuricemic mice. Further research shows that the *Liriodendron chinense* (Hemsl.) Sarg. plays a role in reducing the serum uric acid level by promoting renal uric acid excretion. The use of the present disclosure can provide a new medicament choice for clinical treatment of hyperuricemia and hyperuricemic nephropathy caused by the hyperuricemia.

BRIEF DESCRIPTION OF DRAWINGS

FIG. 4 is a diagram of detection results of expression quantities of collagen fiber 1, fibronectin, and α-smooth muscle actin of the kidneys of the mice in Embodiment 2; and FIG. 5 is a diagram of detection results of uric acid excretion quantities in the 24-hour urine of the mice in Embodiment 3.

DETAILED DESCRIPTION OF EMBODIMENTS

The solution of the present disclosure will be explained below in combination with embodiments. Those skilled in the art will understand that the following embodiments are only used to illustrate the present disclosure and should not be construed as limiting the scope of the present disclosure. The contents in the embodiments in which the specific technology or condition are not indicated shall be carried out according to the technology or condition described in the literatures in the art or according to the product specification. The reagents or instruments used without the manufacturer's indication are all conventional products that are commercially available.

Preparation of an extract of *Liriodendron chinense* (Hemsl.) Sarg.: adding 500 g of the *Liriodendron chinense* (Hemsl.) Sarg. (including bark, branch, and leaf parts) into 5 L of 75% v/v aqueous ethanol solution, boiling for 3 hours, filtering, and evaporating the solvent to dryness, thus obtaining a brown solid extract.

Figure 1:
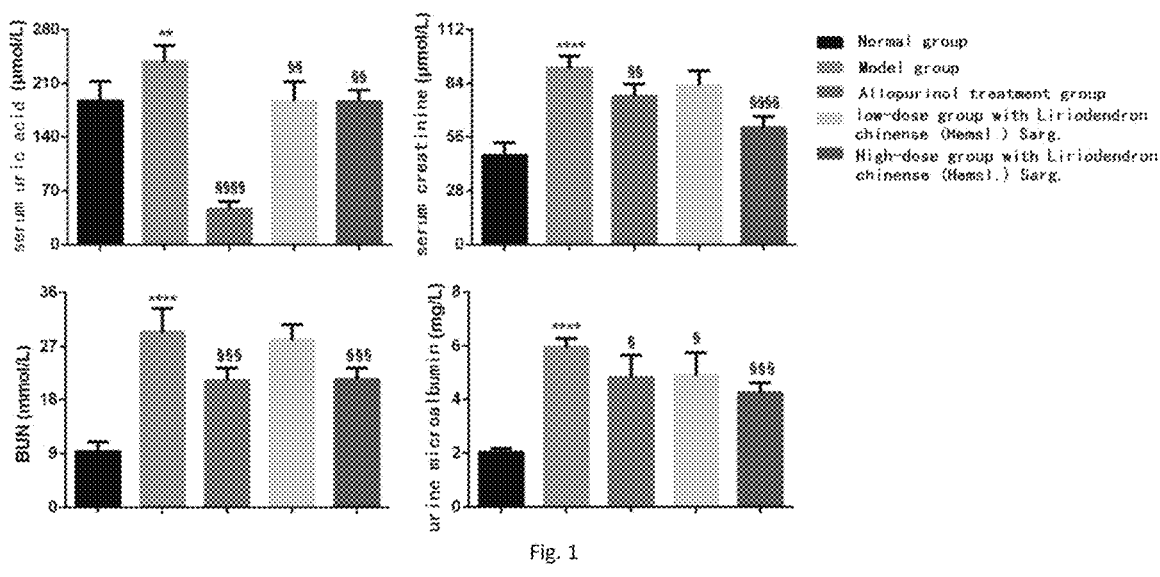
FIG. 1 is a diagram of detection results of serum creatinine, serum uric acid, blood urea nitrogen and urine microalbumin of mice in Embodiment 1.

Experimental methods: male C57BL/6 mice are randomly divided into a normal group, a model group, a positive control group (allopurinol 10 mg/kg/d), a low-dose treatment group (250 mg/kg/d) with the extract of the *Liriodendron chinense* (Hemsl.) Sarg., and a high-dose treatment group (500 mg/kg/d) with the extract of the *Liriodendron chinense* (Hemsl.) Sarg., with 6 mice in each group. The mice in the model group and each treatment group are given a gavage of adenine (160 mg/kg/d) and oteracil potassium (2400 mg/kg/d) for model establishing, while the normal group is given a gavage of an equal volume of double distilled water. The model establishing lasts for 3 weeks. During the model establishing, each treatment group is given a gavage of the extract of the *Liriodendron chinense* (Hemsl.) Sarg. and the allopurinol, and the normal group and the model group are given a gavage of an equal volume of double distilled water. The treatment lasts for 3 weeks. On the 21st day, 24-hour urine of the mice is collected by metabolic cages, and then the mice are sacrificed Embodiment 1. Effects of *Liriodendron chinense* (Hemsl.) Sarg. on reducing serum uric acid and preventing and treating uric acid nephropathy Blood samples of mice are centrifuged for 15 min at 3000 r/min at a room temperature, and then serums are taken for measuring biochemical indicators. Urine samples of the mice are centrifuged for 10 min at 800 g/min at the room temperature, and then upper-layer urine is taken for measuring a level of urine microalbumin. Serum creatinine and Blood Urea Nitrogen (BUN) are detected by using an automatic biochemical analyzer (TC6010L, Jiangxi Tecom Technology Co., Ltd.); and serum uric acid and urine microalbumin are detected by using an automatic biochemical analyzer (BS-240, Shenzhen Mindray Bio-Medical Electronics Co., Ltd.). Experimental results are shown in FIG. 1. PAS staining is conducted on kidney tissues of the mice, and results are shown in FIG. 2.

As can be seen from FIG. 1, the *Liriodendron chinense* (Hemsl.) Sarg. can significantly reduce a serum uric acid level and improve renal functions (reducing levels of the serum creatinine, the BUN and the urine microalbumin). Moreover, the relieving effect on the serum creatinine, the BUN and the urine microalbumin in the high-dose treatment group with the *Liriodendron chinense* (Hemsl.) Sarg. is significantly better than that in the low-dose treatment group (P<0.01, and **P<0.0001 compared with the normal group; $^{\S}$P<0.05, $^{\S\S}$P<0.01, $^{\S\S\S}$P<0.001, and $^{\S\S\S\S P<}$0.0001 compared with the model group).

Figure 2:
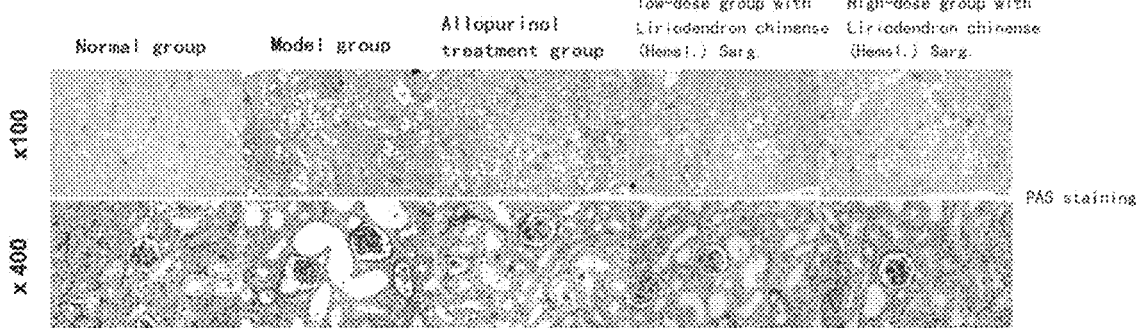
FIG. 2 is a diagram of PAS staining of kidney tissues of the mice in Embodiment 1.

As can be seen from FIG. 2, after treatment with the *Liriodendron chinense* (Hemsl.) Sarg., renal tubular dilation and glomerulosclerosis of kidneys of the hyperuricemic mice are significantly relieved.

Figure 3:
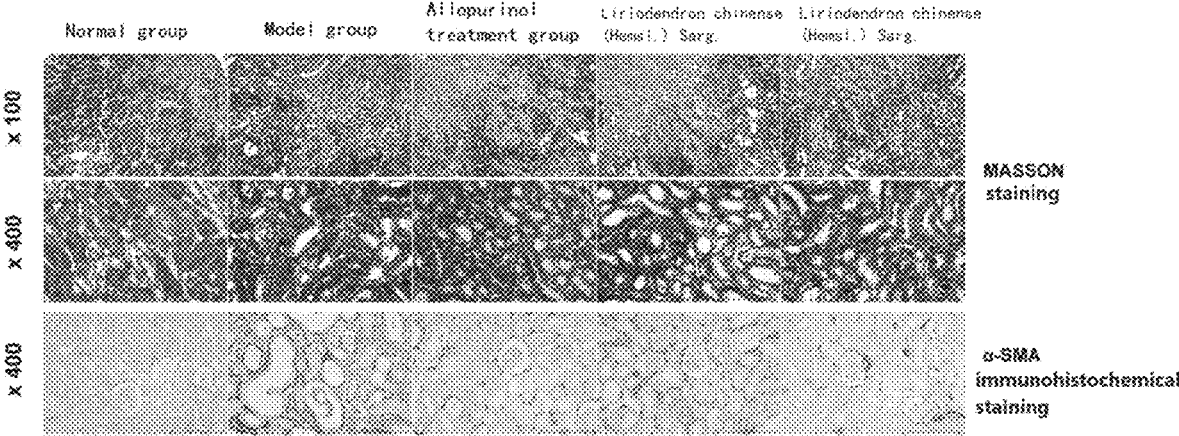
FIG. 3 is a diagram of MASSON staining and α-smooth muscle actin immunohistochemical staining of kidneys of the mice in Embodiment 2.

Embodiment 2. Relieving effect of *Liriodendron chinense* (Hemsl.) Sarg. on chronic uric acid renal fibrosis The expression of collagen fibers of kidneys is evaluated by MASSON staining. Meanwhile, α-smooth muscle actin (α-SMA) immunohistochemical staining is conducted on the kidneys. Experimental results are shown in FIG. 3. Results of Western blot of the kidneys are shown in FIG. 4.

As can be seen from FIG. 3, after treatment with the *Liriodendron chinense* (Hemsl.) Sarg., a degree of renal interstitial fibrosis of hyperuricemic mice is significantly relieved. α-SMA immunohistochemical staining shows that the *Liriodendron chinense* (Hemsl.) Sarg. can effectively inhibit expression of interstitial α-SMA.

As can be seen from FIG. 4, expressions of collagen fiber 1, fibronectin, and α-smooth muscle actin of the kidneys of the hyperuricemic mice are significantly increased, and after treatment with the *Liriodendron chinense* (Hemsl.) Sarg., their expressions in the kidneys can be significantly reduced.

Embodiment 3. *Liriodendron chinense* (Hemsl.) Sarg. reduces a serum uric acid level by promoting renal uric acid excretion On the 21st day of the experiment, 24-hour urine of mice is collected by metabolic cages, and urine volumes are recorded. Urine samples of the mice are centrifuged for 10 min at 800 g/min at a room temperature, and then upper-layer urine is taken for measuring a uric acid level in the urine with an automatic biochemical analyzer (BS-240, Shenzhen Mindray Bio-Medical Electronics Co., Ltd.). Uric acid excretion quantity in the 24-hour urine=24-hour urine volume×uric acid concentration in the 24-hour urine. Experimental results are shown in FIG. 5.

As can be seen from FIG. 5, the uric acid excretion quantity in the 24-hour urine of the mice in the model group is significantly decreased (P<0.0001 compared with a normal group). After treatment with the *Liriodendron chinense* (Hemsl.) Sarg., the uric acid excretion quantity in the urine is significantly increased, and the high-dose group (P<0.000) compared with the model group) is better than the low-dose group (P<0.01 compared with the model group).

The above results show that the *Liriodendron chinense* (Hemsl.) Sarg. reduces the serum uric acid level by promoting renal uric acid excretion.

What is claimed is:

1. A method for reducing a serum uric acid level or for treating or preventing uric acid nephropathy, comprising administering a subject in need thereof an extract of *Liriodendron chinense* (Hemsl.) Sarg (over 500 mg/kg/d) to relieve a degree of renal interstitial fibrosis of hyperuricemia or to inhibit the expression of α-SMA and to promote renal uric acid excretion, wherein the extract is prepared by adding *Liriodendron chinense* (Hemsl.) Sarg. into 75% v/v alcohol for extraction.

2. The method according to claim 1, wherein the extract of *Liriodendron chinense* (Hemsl.) Sarg is in a formulation prepared by using *Liriodendron chinense* (Hemsl.) Sarg. as an active ingredient and adding pharmaceutically acceptable adjuvants or auxiliary ingredients.

3. The method according to claim 2, wherein the formulation is an oral formulation or an injectable formulation.

4. The method according to claim 3, wherein the extract of *Liriodendron chinense* (Hemsl.) Sarg is obtained from at least one of *Liriodendron chinense* (Hemsl.) Sarg. roots, bark, branches, or leaves.

5. The method according to claim 4, wherein the extract is an alcohol extract; the alcohol is $C_1$ to $C_6$ fatty alcohol.

6. The method according to claim 5, wherein a preparation method of the extract comprises the following steps:

adding the *Liriodendron chinense* (Hemsl.) Sarg. into an aqueous ethanol solution for extraction, and concentrating a extracting solution, thus obtaining the extract.

7. The method according to claim 6, wherein the extraction satisfies at least one of the following:

adding into 75% v/v aqueous ethanol solution for extraction;

allowing the solid-liquid ratio to be 500 g/5 L; or performing extracting for 3 hours under a boiling condition.

8. The method according to claim 1, wherein the extract of *Liriodendron chinense* (Hemsl.) Sarg satisfies at least one of the follows:

reduces a level of at least one of serum creatinine, serum uric acid, blood urea nitrogen, or urine microalbumin;

relieves renal tubular dilation and/or glomerulosclerosis;

relieves renal fibrosis; or reduces an expression quantity of at least one of collagen fiber 1, fibronectin, or α-smooth muscle actin in a kidney.

9. The method according to claim 1, wherein the extract of *Liriodendron chinense* (Hemsl.) Sarg is obtained from at least one of *Liriodendron chinense* (Hemsl.) Sarg roots, bark, branches, or leaves.

10. The method according to claim 9, wherein the extract is an alcohol extract wherein the alcohol is $C_1$ to $C_6$ fatty alcohol.

11. The method according to claim 10, wherein the alcohol is ethanol.

12. The method according to claim 11, wherein the method of preparing the extract comprises the following steps: adding the *Liriodendron chinense* (Hemsl.) Sarg. into an aqueous ethanol solution for extraction, and concentrating a extracting solution, thus obtaining the extract.

13. The method according to claim 12, wherein the extraction satisfies at least one of the following:

adding into 75% v/v aqueous ethanol solution for extraction;

allowing the solid-liquid ratio to be 500 g/5 L; or performing extracting for 3 hours under a boiling condition.

14. The method according to claim 4, wherein the alcohol is ethanol.

* * * * *